United States Patent
Gafner et al.

(10) Patent No.: US 7,138,806 B2
(45) Date of Patent: Nov. 21, 2006

(54) POSITION DETECTION

(75) Inventors: Simone Gafner, Langenthal (CH); Michael Krieftewirth, Bern (CH); Beat Steffen, Saanen (CH); Julian Yeandel, Grosshoechstetten (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/754,185

(22) Filed: Jan. 9, 2004

(65) Prior Publication Data

US 2004/0207385 A1   Oct. 21, 2004

Related U.S. Application Data

(63) Continuation of application No. PCT/CH02/00357, filed on Jul. 2, 2002.

(30) Foreign Application Priority Data

Jul. 9, 2001   (DE) ................. 101 33 216

(51) Int. Cl.
G01R 27/26   (2006.01)
A61M 31/00   (2006.01)
(52) U.S. Cl. .............. 324/660; 324/661; 604/67
(58) Field of Classification Search .......... 324/661, 324/658, 649, 600, 519, 686, 660; 604/97.02, 604/118, 502, 19, 21, 65, 67; 600/1, 3, 7
See application file for complete search history.

(56) References Cited

U.S. PATENT DOCUMENTS

| | | | | |
|---|---|---|---|---|
| 3,961,318 A | * | 6/1976 | Farrand et al. ............. 324/660 |
| 4,462,760 A | * | 7/1984 | Sarich et al. .................. 417/54 |
| 4,562,430 A | * | 12/1985 | Robinson ..................... 324/660 |
| 4,630,047 A | * | 12/1986 | Tanaka et al. ............... 324/660 |
| 4,658,830 A | * | 4/1987 | Sarnoff ........................ 600/509 |
| 4,694,235 A | | 9/1987 | Flowers |
| 4,998,103 A | * | 3/1991 | Rosswurm et al. .... 340/870.37 |
| 5,077,635 A | | 12/1991 | Bolhagen et al. |
| 5,239,307 A | * | 8/1993 | Andermo ............... 340/870.37 |
| 5,410,232 A | * | 4/1995 | Lee ........................ 318/568.11 |
| 5,497,101 A | * | 3/1996 | Fillion ......................... 324/662 |
| 5,513,539 A | * | 5/1996 | McLaughlin et al. ....... 73/865.9 |
| 5,557,596 A | * | 9/1996 | Gibson et al. .............. 369/101 |
| 5,611,784 A | * | 3/1997 | Barresi et al. .............. 604/211 |
| 5,691,646 A | * | 11/1997 | Sasaki ........................ 324/662 |
| 5,920,198 A | * | 7/1999 | Suzuki et al. ............... 324/662 |
| 6,339,336 B1 | * | 1/2002 | Oisugi et al. ................ 324/658 |
| 6,538,227 B1 | * | 3/2003 | Sano et al. ................. 219/69.2 |
| 6,747,462 B1 | * | 6/2004 | Fasen et al. ................. 324/662 |
| 7,025,757 B1 | * | 4/2006 | Reilly et al. ................ 604/506 |
| 7,029,455 B1 | * | 4/2006 | Flaherty ..................... 604/131 |
| 7,041,048 B1 | * | 5/2006 | Drobnik et al. ................. 600/7 |

FOREIGN PATENT DOCUMENTS

DE   4234016   4/1993

* cited by examiner

*Primary Examiner*—Anjan Deb
*Assistant Examiner*—Hoai-An D. Nguyen
(74) *Attorney, Agent, or Firm*—Dorsey & Whitney LLP

(57) ABSTRACT

The invention relates to a device for detecting the position of a rotor relative to a stator, wherein at least one electrode is arranged on the rotor and at least one electrode is arranged on the stator, such that the electrodes at least partially overlap in at least one rotational position of the rotor relative to the stator, and encompasses a method for measuring the rotational position of a rotor including at least one rotor electrode relative to a stator including at least one stator electrode, wherein the rotational position is detected using a capacitive coupling between the rotor electrode and the stator electrode.

9 Claims, 8 Drawing Sheets

POSITION DETECTION

CROSS-REFERENCE TO RELATED APPLICATION(S)

This application is a continuation of and claims priority to International Application No. PCT/CH02/00357, filed on Jul. 2, 2002, which claims priority to German Application No. 10133216.5, filed on Jul. 9, 2001, the contents of both of which are incorporated herein by reference in their entirety.

BACKGROUND

The present invention relates to a device and a method for detecting the position of one element relative to another element, in particular for detecting the position of a rotor relative to a stator.

More particularly, in some embodiments, the invention relates to a device for dispensing a liquid in doses, in particular in the area of medicine, e.g., an infusion or injection apparatus, wherein the set dosage of the dispensed liquid or liquid to be dispensed can be ascertained by the position of a rotor, such as a threaded rod, relative to a stator, such as a casing, device body, or portion of an injection device, including those known as injection "pens". In general, a dosage to be dispensed by a pen is set by turning for example a dosing button and dispensed by then pressing the dosing button.

In order to dose a liquid—for example insulin, hormone preparations or the like—to be dispensed from a medical injection instrument or device as exactly as possible, it is necessary to be able to monitor the process of setting a dosage, in order—for example, in the event of an incorrect dosage—to output a warning signal or to prevent the dosage from being dispensed. Since the dosage is usually set by turning a rotor situated in a casing of device pen, the rotor generally being provided with a thread, the advance of the rotor can be ascertained from the turns made in order to set the dosage, and a dosage to be dispensed or a dispensed dosage thus determined.

Known devices for measuring this turning movement are based on mechanical principles and are therefore costly and relatively imprecise.

SUMMARY

It is an object of the present invention to provide an injection device comprising relatively positionable elements and means associated with the relatively positionable elements for providing sensing characteristics, wherein a change in provided sensing characteristics reflects the relative position of the relatively positionable elements.

It is an object of the present invention to provide embodiments of a device and a method for detecting the position of a first element, for example a rotor, relative to a second element, for example a stator, wherein the device can be easily and cost effectively made, and enables the position to be detected very precisely.

A rotor is understood in the sense of the invention as a rotating element which can be moved or shifted in its rotational position and/or axial position relative to a stator. In the sense of the invention, the terms rotor and stator are to be understood such that these two elements can be moved relative to each other, irrespective of whether only the rotor is moved, or only the stator, or both elements simultaneously. In order to simplify the description, a rotor lying in the stator shall be assumed in the following, wherein, however, the rotor need not be completely surrounded by the stator and can even lie outside the stator and, as applicable, surround it.

The device in accordance with the invention for detecting the position of a rotor relative to a stator comprises at least one electrode arranged on the rotor. The electrode can lie on the outer surface of the rotor and/or be partially or completely embedded in the rotor, wherein for example a dielectric can be provided on the electrode. Furthermore, at least one electrode is provided on the stator, wherein said electrode can likewise be freely accessible or coated with suitable layers of the material forming the stator or another suitable material. The arrangement of the electrodes on the rotor and the stator in accordance with the invention is thus such that when the rotor and the stator move relative to each other, in particular when the rotor rotates relative to the stator, the respective electrodes at least partially overlap given a particular relative position of the rotor and the stator, such that the electrodes are operably and/or capacitively coupled. The position of the rotor relative to the stator can be ascertained from this capacitive coupling between the at least one rotor electrode and the at least one stator electrode, for example by ascertaining from the degree of overlap between the respective electrodes and the capacitive coupling which changes in accordance with the relative position relative of the rotor and stator. The electrodes are preferably fixedly connected to the rotor and the stator.

In principle, a multitude of embodiments are conceivable for the geometries of the rotor and stator electrode; some preferred embodiments enable an absolute statement of a rotational angle of the rotor relative to the stator. To this end, the rotor and/or stator electrode can be formed such with a different width depending on the position on the circumference. The rotor electrode can, in one exemplary embodiment, have the form of an equilateral triangle which is laid around the outer side of a cylindrical rotor such that the base side of the triangle runs parallel to the longitudinal axis of the rotor and the tip of the triangle encircling the circumference of the rotor abuts the base side of the triangle again. Such an electrode exhibits a width which constantly changes around the circumference of the rotor. If a stator electrode extending over only a part of the stator is laid opposite such a rotor electrode, then the result is a capacitive coupling which changes linearly depending on the relative rotational position, such that the angular position of the rotor relative to the stator can be ascertained on the basis of the measured capacitive coupling of said electrodes.

The position of the rotor can also, however, be detected with simpler geometries of the electrodes, for example by arranging electrodes on the rotor and/or stator equidistantly around the circumference.

Other embodiments of the invention are also conceivable which use more than just one electrode on the rotor and/or stator, in order to be able to detect the position more precisely or more easily. In particular, it is advantageous to provide at least two electrodes on the stator, which can be coupled to at least one electrode on the rotor, since the rotor electrode is then capacitively coupled to one or both stator electrodes depending on the rotational position and a measurement can thus be taken without connecting the rotationally mounted rotor electrode to the stator electrodes, for example by means of sliding contacts. The rotor can thus be rotationally mounted without direct electrical contact, wherein the position can be detected solely on the basis of the capacitive coupling between the at least one rotor electrode and the at least two stator electrodes.

In some embodiments, the rotor and stator electrodes are preferably arranged such that a capacitor bridge structure can therefore be realized. A capacitor bridge is described in general terms with reference to FIG. 1.

FIG. 1 shows two capacitors C1 and C2 connected in series, wherein the total voltage across both capacitors is $V_{total}=V_1+V_2$; $V_1$ and $V_2$ are the falling voltages at the respective capacitors C1 and C2. For the ratio of voltage $V_1$ to the total voltage $V_{total}$, it holds that:

$$V_1/V_{total}=C2/(C1+C2) \qquad \text{Equation (1)}$$

The device in accordance with the invention is advantageously designed such that one of the capacitors of the capacitor bridge is formed by the capacitively coupled rotor and stator electrodes, wherein furthermore a reference capacitor is provided. The reference capacitor can be provided externally, for example on the stator, or formed by other rotor and stator electrodes. It is in particular advantageous to connect one side of the reference capacitor to a stator electrode, so as to have to attach as few electrical connections as possible to the rotating rotor.

It may be seen from the above equation that changing the capacity of one of two capacitors connected in series changes the voltage at said capacitor. By using a reference capacitor, measuring the capacity or change in capacity can be simplified, by measuring the voltage in a known way. If rotor and stator electrodes are suitably arranged and formed, it is not even necessary to measure the absolute value of the voltage at an electrode or capacitor in order to be able to determine the position. It can be sufficient to compare the voltage at an electrode or capacitor with a reference value, for example by means of a comparator or other suitable device, and thus obtain a statement as to whether the voltage at the capacitor or the potential of a capacitor electrode is above or below the reference value. This is particularly advantageous since the elements used in medical instruments are relatively small and consequently the changes in capacity which occur when the rotor and stator electrode move relative to each other are also relatively small, in the picofarad range. If, for example, a change in capacity is measured by comparing a changing voltage with a reference value and outputting a binary signal indicating whether the voltage is above or below the reference value, then it is not necessary to determine the absolute value of the change in capacity. This can simplify measuring. If rotor and stator electrodes are suitably arranged and formed, a statement of a rotational position or rotational direction can be obtained from binary signals generated in this way.

In some preferred embodiments, two, three, four or more electrodes are provided on the rotor and/or stator which can be offset with respect to each other in the radial and/or axial direction, in order to enable various capacitive couplings depending on the position of the rotor relative to the stator, on the basis of which the relative position can be determined. In this way, individual electrodes can be formed such that a substantially constant coupling can always be maintained irrespective of the relative position of the rotor and stator, in order to couple particular, constant voltages. The individual electrodes preferably then exhibit a different geometry depending on their function, wherein for example electrodes can be provided on the rotor and/or stator which have an axial extension or width which differs in length for a defined length in the circumferential direction. Electrodes can also be formed such that they extend around the entire circumference of the rotor and/or the stator, with a constant or changing width.

In a preferred embodiment of the invention, the rotor electrodes are formed relatively simply, for example as two mutually opposing, partial annular or semi-annular elements which are electrically separated from each other and arranged on the circumference of a substantially cylindrical rotor. On the inner surface of the stator, opposite the outer circumference of the rotor and preferably having a substantially constant distance from the outer surface of the rotor, two, three, four or more electrodes are provided, distributed in the circumferential direction of the stator, preferably distributed equally around the rotational axis of the rotor or symmetrically with respect to the rotational axis of the rotor. The stator electrodes can also have different surfaces to each other, respectively or in pairs, in order to thus enable various capacitive couplings depending on the position of the rotor electrodes relative to the stator electrodes. In this way, the rotor can be formed relatively simply, wherein the stator or stator electrodes is/are formed comparatively more complexly. In such an embodiment, care should be taken that single valued statements of the rotational position of the rotor relative to the stator are possible.

In accordance with another preferred embodiment of the invention, the opposite approach is taken, i.e., the stator electrodes are designed relatively simply while the rotor electrodes exhibit a more complex structure. In this way, for example, two electrodes can be provided on the stator which can be capacitively coupled to a plurality of electrodes on the rotor, depending on the relative position or rotational position.

In one preferred embodiment, three rotor electrodes are provided, as shown in FIG. 6A, wherein a first rotor electrode comprises an annular section encircling the rotor and a partial annular or semi-annular section connected to it. The partial annular section points towards the second and third rotor electrodes, wherein the third rotor electrode—like the first rotor electrode—comprises an annular section and a partial annular or semi-annular section connected to it which is offset by 180° with respect to the partial annular section of the first electrode and points towards the first electrode. A second electrode is arranged between the first and third electrode and likewise comprises a circumferential annular section with two partial annular or semi-annular sections connected to it, the first partial annular section extending towards the first electrode and the second partial annular section extending towards the second electrode, wherein the two partial annular sections are preferably arranged offset from each other by 180°. The first, second and third rotor electrodes are formed such that these three electrodes can be disposed on a partial area of the stator, almost covering its surface, i.e., the electrodes engage with each other and only a comparatively small, preferably constant section lies between the respective electrodes. It must, however, then be ensured that the individual electrodes are electrically insulated from each other. Electrodes which can be annular or partially annular, so as to consistently enable a capacitive coupling in a defined way for any rotational position, are arranged on the stator opposite the respective circumferential annular areas of the rotor electrodes.

Thus, for example, the first and third electrode can be loaded with a first potential while the second, middle electrode is loaded with a second potential. The first potential can be earth and the second potential a supply voltage of, for example, 5 V. Preferably, two electrode pairs, offset in the axial direction, are arranged on the stator such that said electrode pairs oppose the mutually engaging partial annular areas of the rotor electrodes. Advantageously, the first and second partial annular areas of the second rotor electrode exhibit a different length according to the respectively opposing partial annular areas, offset by 180°, of the first and third rotor electrode, said length approximately corresponding to the respective length of the respectively assigned stator electrode pairs. In some embodiments, the individual elements of the stator electrodes are particularly preferably arranged offset by about 90° with respect to each other, wherein the elements of one stator electrode pair are advantageously in an axial extension with respect to the elements of the other electrode pair. The arrangement shown in FIG. 6A enables a relatively large overlap of the respective electrode surfaces for various rotational positions, in order to obtain as large a capacitive coupling between the rotor and stator electrodes as possible.

In some embodiments, at least one locking position of the rotor relative to the stator is provided, in which the rotor is for example in a defined position following a setting process. Advantageously, a number of locking positions are provided, in particular at constant distances, which can suitably lock the rotor such that at least one rotor and/or stator electrode opposes another electrode of the stator or rotor in the transition to an adjacent locking position, so as to reverse the polarity of at least one electrode.

In accordance with another aspect of the invention, which may also be used independently of the embodiments described above, a shift or a position of a shifting element, for example the rotor, relative to the stator in the longitudinal direction is detected. It is not then necessary for a rotational movement to be performed.

Such relative movements occur in particular when administering a liquid by means of a pen by pressing the dosing button, which causes the rotor or a threaded rod to shift in the axial direction. In order to detect whether the axial movement of the rotor or threaded rod is sufficient to administer a required and/or set amount, detecting the axial movement of a rotor or threaded rod is proposed in accordance with the invention.

In accordance with one embodiment, the position can be detected by means of a pressure and/or force sensor onto which an element, such as a rod or spring, coupled to the shifting element, e.g., the dosing button or the threaded rod, presses. If the axial movement is too small, it can be ascertained on the basis of a voltage signal output by the pressure or force sensor, for example a piezo element, that the axial movement was not yet sufficient to dispense the desired dosage. A warning signal can then be output or the dosage can be prevented from being dispensed.

In accordance with another embodiment, an electrode can be provided which is coupled to the dosing button, the threaded rod or another element which may be shifted in the axial direction. Using this electrode, a voltage can be tapped at a non-shifting electrical resistor depending on the axial shift at a particular position, said voltage being characteristic of a particular position of the dosing button or a threaded rod, in order to ascertain the position from this voltage.

According to another embodiment of the invention, an axially shifting element and an element which is fixed relative to it can be capacitively coupled, wherein the position can be detected on the basis of the change in capacity.

The device in accordance with the invention is advantageously designed such that it is locked or a signal which the user can perceive is output in at least one position, e.g., with the dosing button completely pressed in or in its initial position, so as to indicate that the desired dosage is being dispensed.

In one embodiment of the method in accordance with the invention the method comprising measuring the rotational position of a rotor provided with at least one electrode relative to a stator provided with at least one electrode wherein the rotational position is ascertained from the capacitive coupling between the rotor electrode and the stator electrode. In one embodiment, the capacity can be measured by measuring a charging or discharging current and/or by measuring a voltage.

Preferably, the voltage at a rotor/stator electrode pair is used as the variable to be measured, which is advantageously compared with a reference voltage, for example by means of a comparator. A peak value can thus be detected, wherein when the variable exceeds or falls below a certain limit value, a change in signal occurs and binary signals can thus be generated. This peak value can also be detected when measuring a charging or discharging current of the capacitor formed by the electrodes.

In one preferred embodiment, the electrodes are configured with a corresponding measuring array, such that errors can be recognized and corrected, for example by defining—starting from a measured actual state—only two possible adjacent states which indicate a shift or rotation of the rotor in one direction or the other. If a signal is ascertained which corresponds to an invalid or unavailable state, then an error signal can be output which indicates an error in detecting the position. The error can be corrected as applicable, depending on the permissible measuring signals used.

Advantageously, one or more of the electrodes used can be made of a suitable material, metal or a conductive or magnetizable plastic. Suitable plastics may be produced for example by adding carbon (soot), metal elements, iron powder or the like. Conductive plastics could also be attached in a z-k injection molding method. Thus, in some embodiments, the present invention comprises an injection device comprising relatively positionable elements and means associated with the relatively positionable elements for providing sensing characteristics, wherein a change in provided sensing characteristics reflects the relative position of the relatively positionable elements.

BRIEF DESCRIPTION OF THE DRAWINGS

FIGS. 4A to 4D, is a schematic representation of a third embodiment of the invention, in four different rotational positions;

FIG. 5, including

DETAILED DESCRIPTION

Figure 2C:
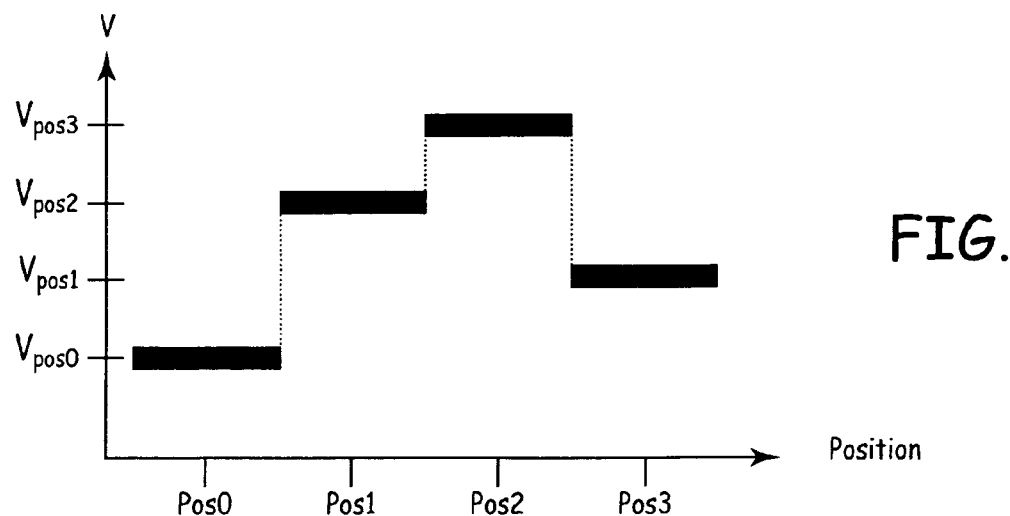
FIG. 2C depicts output signals from measuring the voltage using the device shown in FIG. 2A, for four rotational positions.
Figure 2B:
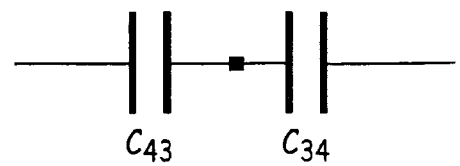
FIG. 2B depicts the equivalent circuit diagram for the arrangement shown in FIG. 2A.
Figure 2A:
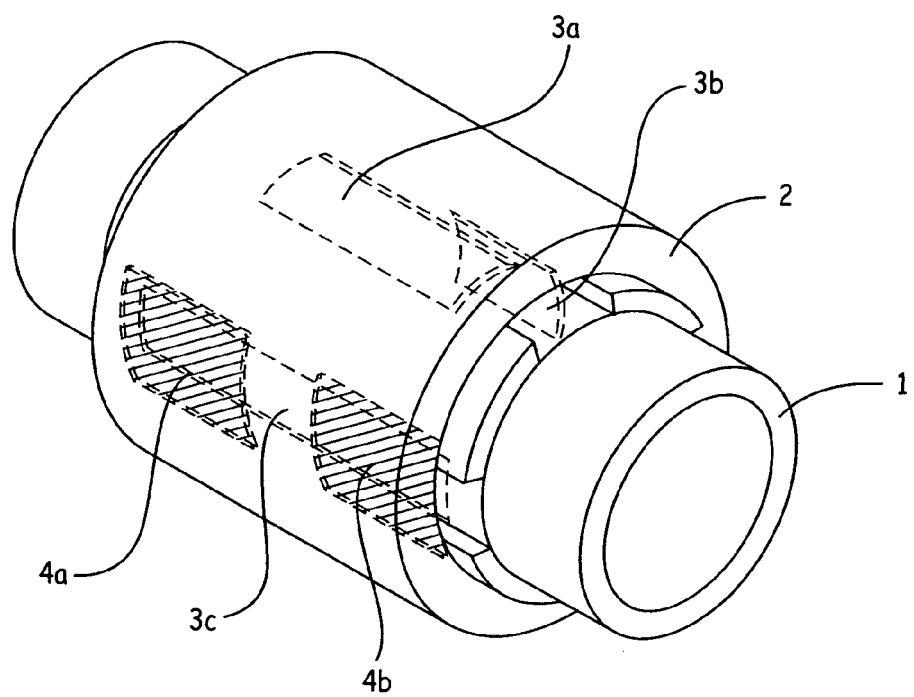
FIG. 2A depicts a rotor-stator arrangement comprising electrodes in accordance with a first embodiment of the invention.

FIG. 2A schematically shows a threaded rod 1 which serves as a rotor in the sense of the invention and is rotationally mounted in a pen or stator 2, wherein four rotor electrodes are arranged on the rotor 1, each offset by 90° in the circumferential direction, of which three rotor electrodes 3a, 3b and 3c can be seen in FIG. 2A. The rotor electrodes exhibit an approximately identical width in the circumferential direction and have four different lengths in the axial direction. The two stator electrodes 4a and 4b are formed substantially identically with respect to their dimensions and are arranged on the inner side of the stator 2 offset in the axial direction. In the position shown in FIG. 2A, the rotor electrode 3c opposes the stator electrodes 4a and 4b and extends in the axial direction approximately from the outer edge of the left-hand stator electrode 4a along its entire axial length up to approximately the right-hand outer edge of the second stator electrode 4b, which provides a relatively good capacitive coupling between the rotor electrode 3c and the stator electrodes 4a and 4b. If the rotor 1 is turned such that the rotor electrode 3a opposes the stator electrodes 4a and 4b, then the capacitive coupling is impaired, since the rotor electrode 3a has as smaller length in the axial direction than the rotor electrode 3c.

Figure 1:
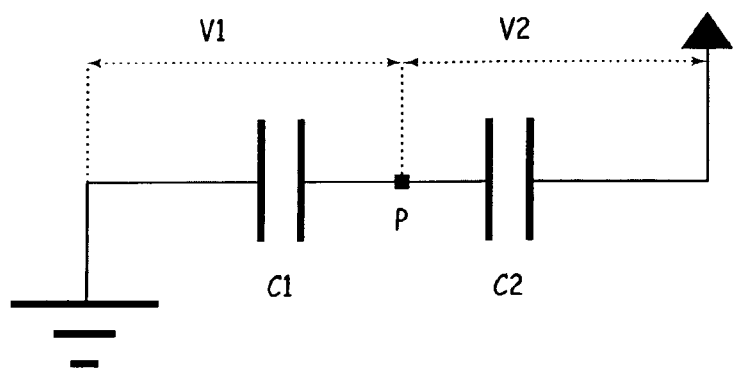
FIG. 1 depicts a capacitor bridge circuit.

FIG. 2B schematically shows the electrical equivalent circuit diagram for the device shown in FIG. 2A, wherein the capacitive coupling between the stator electrode 4a and the rotor electrode 3c can be understood as a first capacitor $C_{43}$ which is connected in series to a second capacitor $C_{34}$ formed by the capacitively coupled electrodes 3c and 4b. If the overlap surface of the rotor and stator electrodes decreases, this represents a reduction in the total capacity formed by the capacitors $C_{43}$ and $C_{34}$, which for example is the case if the shorter rotor electrode 3a opposes the stator electrodes. If this total capacity C1 formed by the capacitors $C_{43}$ and $C_{34}$ is connected in series with a reference capacitor C2, then in accordance with Equation (1) above, the circuit shown in FIG. 1 results in a measuring array using which the progression of voltages shown in FIG. 2C, for the four rotational positions at which the rotor electrodes 3 oppose the stator electrodes 4, is obtained qualitatively at a voltmeter applied to the point P between the capacitors when the rotor 1 is turned in the stator 2, wherein the four respectively different voltage levels are caused by the four rotor electrodes 3 formed with different lengths.

Figure 3:
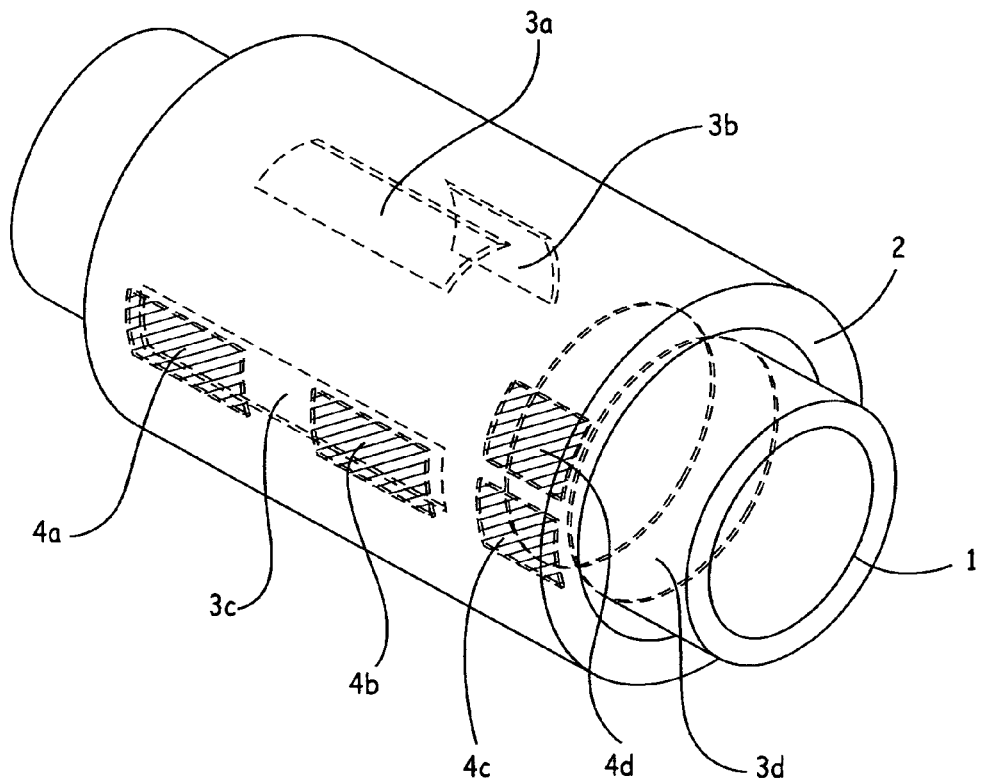
FIG. 3 depicts a rotor-stator arrangement in accordance with a second embodiment of the invention.

FIG. 3 shows a second embodiment of the present invention, wherein—as opposed to the embodiment shown in FIG. 2A—another electrode 3d is provided, formed annularly around the rotor 1 and opposed by two stator electrodes 4c and 4d, offset in the circumferential direction with respect to each other. Using these additional electrodes 3d, 4c and 4d, a reference capacitor C2 can be formed as a series circuit between the capacitor 4c, 3d and the capacitor 3d, 4d, which is connected in series with the capacitor C1 formed by the stator electrodes 4a, 4b and the rotor electrodes 3a to 3c, as shown in FIG. 1. The embodiment shown in FIG. 3 enables a stable measurement due to the low dependence of the voltage measured at the point P on a deviation by the rotor 1 with respect to its coaxial position relative to the stator 2, i.e. if for example due to an irregularity the rotor 1 approaches the stator electrodes 4a and 4b, not only the capacity C1 formed by means of these electrodes increases but also the capacity of the capacitor C2 formed via the stator electrodes 4c and 4d, such that measurement fluctuations can be reduced.

Figure 4:
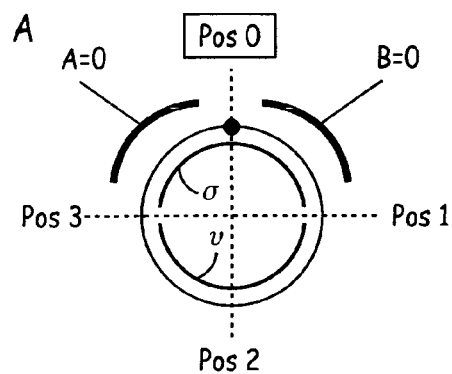
FIG. 4, including
Figure 4:
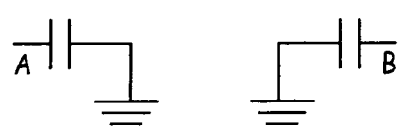
Figure 4:
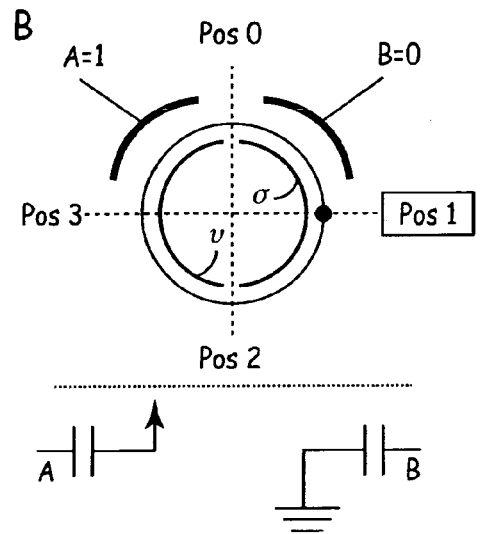
Figure 4:
Figure 4:
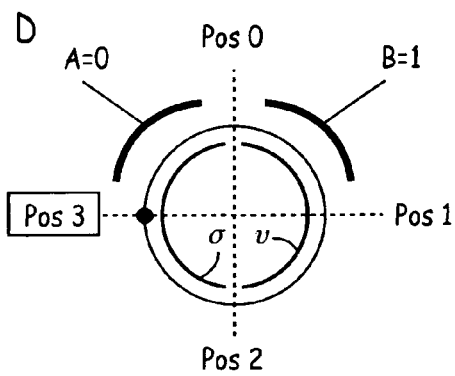
Figure 4:
Figure 4:
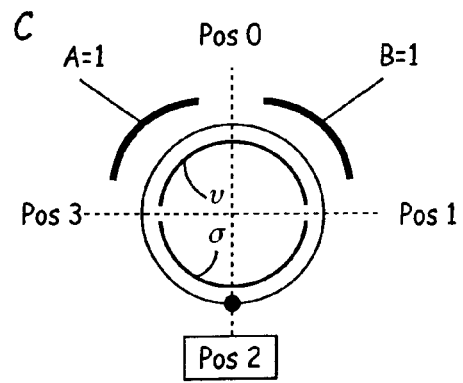
Figure 4:

FIG. 4, including FIGS. 4A to 4D, schematically shows an electrode arrangement in accordance with a third embodiment of the invention, in four different positions rotated by 90° with respect to each other. Below the respective rotational positions, the corresponding electrical circuits of the corresponding capacitors formed by the electrodes are shown. The approximately semi-annular electrodes opposing each other on the rotor are indicated as 0 and V, the electrode 0 having an earth potential and the electrode V having a supply voltage. It may be seen from FIG. 4A that the electrodes A and B arranged on the stator, which are arranged offset by 90° with respect to each other, both oppose the electrode 0 in a first rotational position and are thus both capacitively coupled to a mass potential. Consequently, the result is the electrical equivalent circuit shown under the schematic rotor-stator view, whereby the capacitors formed by the stator electrodes A and B are both at mass on one side.

Figure 7:
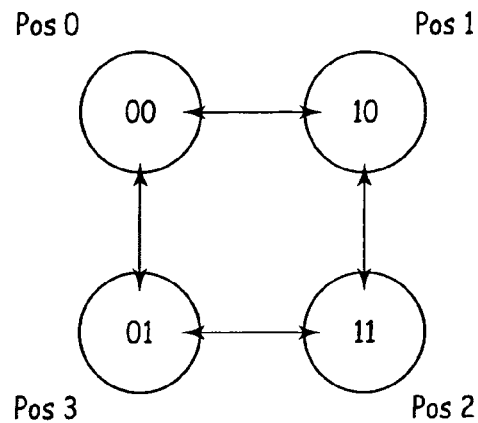
FIG. 7 depicts a state-transition diagram to illustrate error recognition in accordance with the present invention.

If, for example, the potential on the electrodes A and B is compared by means of a comparator with a reference capacitor which is preferably half as large as the potential of the electrode V, then the binary value 0 is applied to the both stator electrodes A and B. If the rotor is turned to the right by 90°, as shown in FIG. 4B, then the stator electrode B still has a potential of 0, while the stator electrode A now opposes the rotor electrode V and is capacitively coupled to it, such that the electrode A has a higher potential, schematically shown by the electrical equivalent circuit diagram. Using a comparator, the binary value I can be obtained for the stator electrode A. If the rotor is turned by a further 90°, the result is the arrangement shown in FIG. 4C, wherein the stator electrodes A and B are both moved to the binary value 1. FIG. 4D shows the state if the rotor is turned by a further 90°, such that the stator electrode A is again at a potential of 0, while the stator electrode B is coupled to the potential of the rotor electrode V. Consequently, a two-digit binary code=AB can be formed, for each of the four rotational positions, from the binary values ascertained by means of the stator electrodes A, B. For a state, for example of the rotational position shown in FIG. 4A, there are only two valid adjacent states, namely the states shown in FIGS. 4B and 4D. A state-transition diagram for the four positions shown in FIGS. 4A to 4D is shown in FIG. 7. The arrows represent the permissible transitions of state, such that, for example, a transition from the state 00 to the state 11 is clearly an error, which can be detected. If the rotor is mechanically configured such that it locks after every turn of 90°, then the stable states shown in FIGS. 4A to 4D are obtained.

Figure 5A:
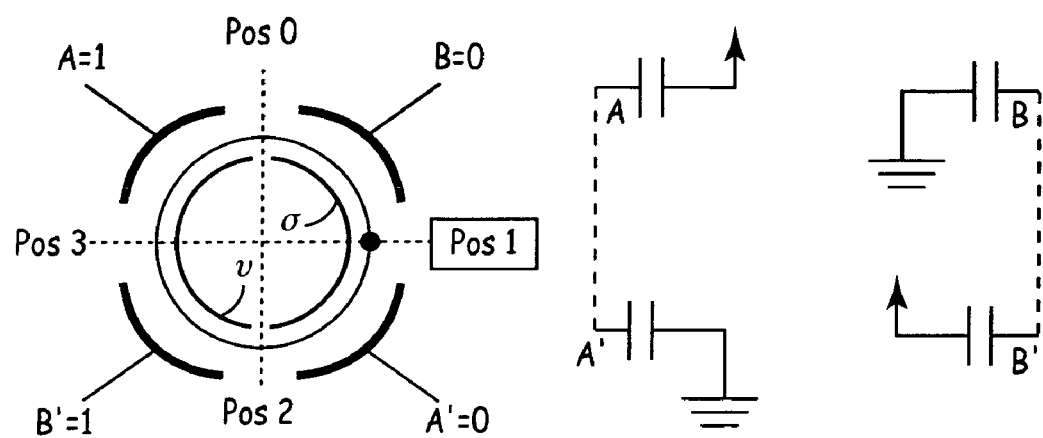
FIGS. 5A and 5B, is a schematic representation of a fourth embodiment of the present invention.
Figure 5B:
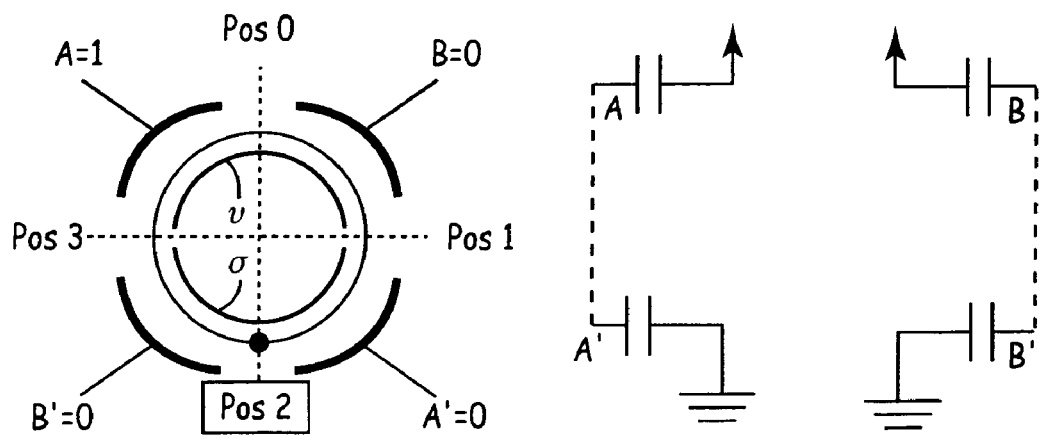

FIGS. 5A and 5B show a fourth embodiment of the present invention, wherein other than in the third embodiment shown in FIG. 4, four stator electrodes A, B, A' and B' are provided which are each arranged offset by about 90°. If the electrodes A and A', and the electrodes B and B', are electrically connected to each other, as shown in the adjacent electrical equivalent circuit diagrams, then a capacitor bridge circuit can be formed. If the surfaces of the electrodes A, B are different to the surfaces of the electrodes A', B', then the different rotational positions of the rotor can be clearly detected. If the rotor is turned to the right by 90°, from the position I shown in FIG. 5A and indicated by the point P to the position 2, then the result is no change in the electrical circuit with respect to the electrodes A, A'. With respect to the electrodes B, B', however, the polarities are reversed, which can be measured and/or converted into a binary signal by means of a comparator.

Although various embodiments of binary coding have been described by way of example, it is noted that a multitude of other embodiments of the invention are conceivable which, for example use a multi-digit code, wherein the number and position of the rotor and/or stator electrodes can be changed.

Figure 6A:
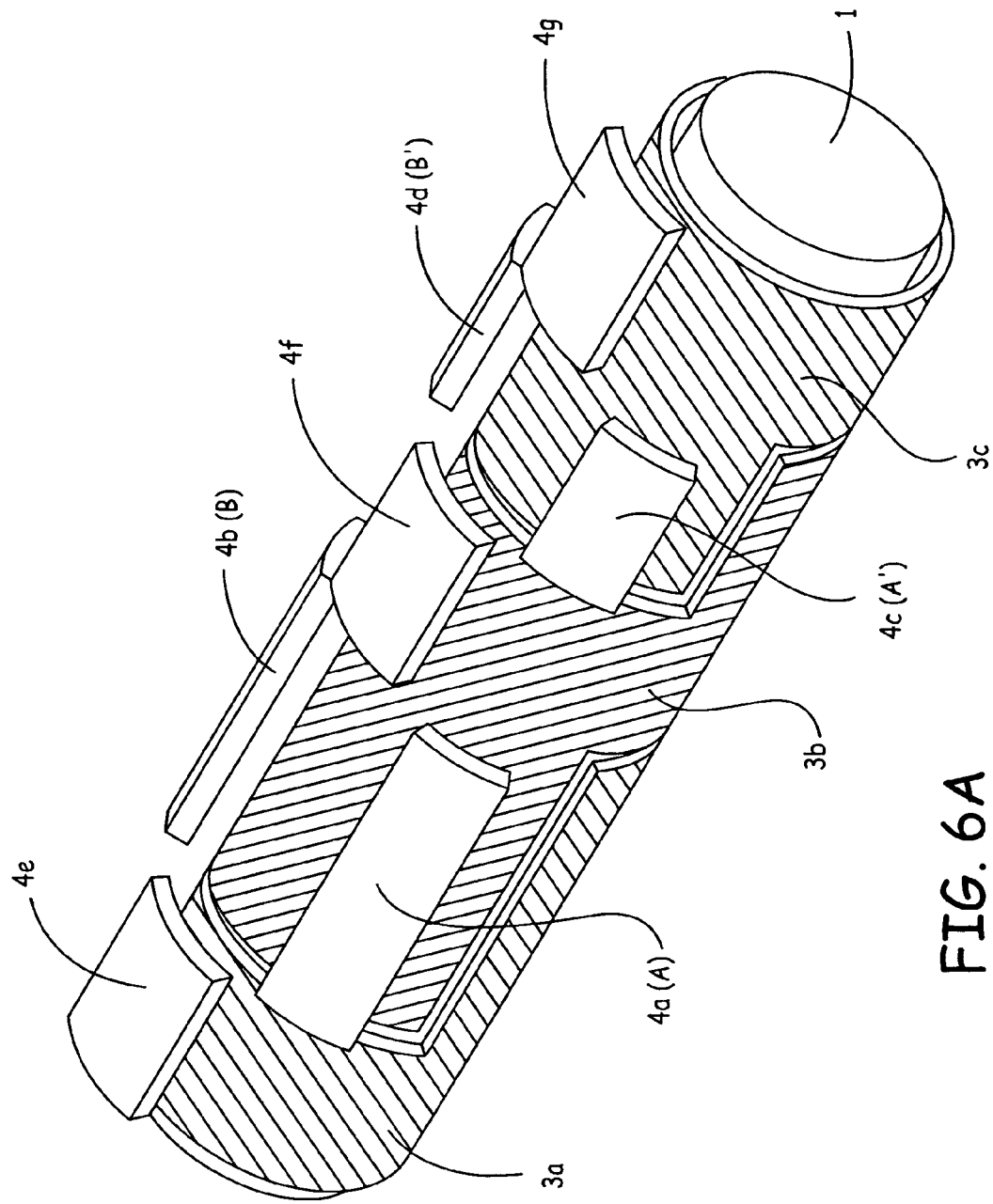
FIG. 6A depicts a device in accordance with a fifth embodiment of the present invention.
Figure 6B:
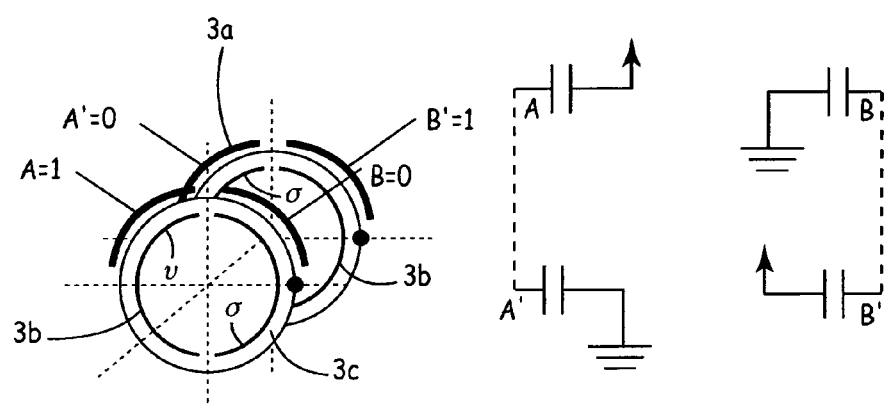
FIG. 6B is a schematic representation of the device shown in FIG. 6A.

FIG. 6A shows a fifth embodiment of the present invention, wherein three rotor electrodes 3a, 3b, 3c are provided and wherein the electrodes each comprise an annular element which opposes the stator electrodes 4e, 4f and 4g, wherein on each of the electrodes 3a and 3c, a semi-annular electrode element is also provided which opposes corresponding semi-annular electrode elements of the electrode 3b on the rotor, the semi-annular electrode elements of the electrodes 3a and 3c exhibiting different lengths, corresponding to the semi-annular electrode elements of the electrode 3b. The electrode pairs 4a, 4b and 4c, 4d are provided on the stator in accordance with said different lengths, and are offset from each other in the axial direction, being respectively arranged turned by about 90° from each other. By means of the electrodes 4e, 4f and 4g, a voltage can be constantly coupled into the rotor electrodes 3a, 3b and 3c for any rotational position of the rotor 1. The stator electrodes 4a, 4b and 4c, 4d can be ascertained in order to measure the rotational position of the rotor 1, since the preferably differently polarized semi-annular elements of the respective rotor electrodes respectively oppose said electrodes, depending on the rotational position. The device shown in FIG. 6A is particularly advantageous due to the large surface overlap of the electrodes, since this enables strong capacitive couplings, which results in a greater signal strength. As may be seen from the schematic arrangement in FIG. 6B, the outer rotor electrodes 3a and 3c are coupled to a mass potential by means of the stator electrodes 4e and 4g, while the rotor electrode 3b is coupled to a supply voltage via the stator electrode 4f. In the arrangement shown in FIG. 6A, the electrodes 4a, 4c, 4b, 4d are indicated for simplicity by A, A', B and B'. The rotor electrodes 3a, 3b and 3c are arranged such that the stator electrodes A and A' on the one hand, and B and B' on the other, each oppose oppositely polarized rotor electrodes. Rotation of the rotor can in turn be recognized by measuring or converting the potentials at the stator electrodes A, A', B and B'.

Figure 8:
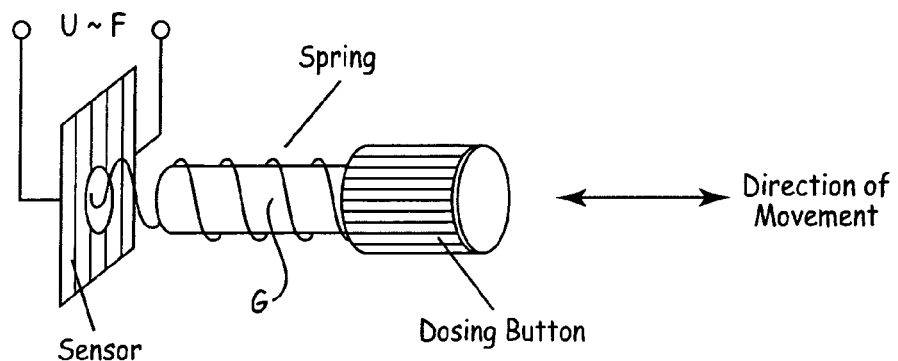
FIG. 8 depicts a first embodiment of a device for detecting a longitudinal movement.

FIG. 8 shows one embodiment of another aspect of the present invention for detecting the longitudinal movement of a shifting element, e.g., a rotor or threaded rod. Usually, for example in the case of an injection pen, a dosage to be dispensed is firstly set by means of a turning movement, which can be detected as described above, whereupon the set dosage is dispensed by means of an axial or longitudinal movement, by pressing onto the dosing button D. In accordance with the invention, the dosing button D is connected to a spiral spring S which presses onto the force sensor K. From the force measured by the force sensor K, the path traveled by the dosing button in the movement direction shown by the arrow can be deduced, the force being greater the further the button is pressed. In this respect, for example, a force F measured by the force sensor K can be converted into a voltage U which can be compared with a reference value by means of a suitable comparator C. If it established that a particular limit value has not been exceeded by the force F measured by means of the force sensor K, then a warning signal can be output which indicates that the set dosage has not been dispensed or not completely dispensed.

Figure 9:
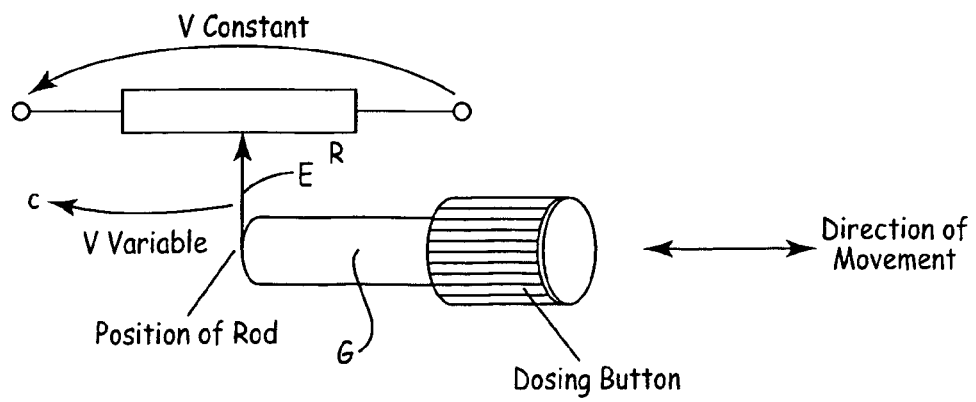
FIG. 9 depicts a second embodiment of a device for detecting a longitudinal movement.

FIG. 9 shows an alternative to the embodiment shown in FIG. 8, wherein an electrical resistor R is arranged running parallel to the dosing button D or the threaded rod G and can for example be arranged on the inner side of a casing shell. A tapped electrode E connected to the threaded rod G or dosing button D is shifted along the resistor R by a longitudinal movement. If the potential of the tapped electrode E with respect to one of the end points of the resistor R is measured, then the absolute position of the dosing button or threaded rod can be ascertained from this potential, which allows the dispensed amount of medicine to be deduced.

In general terms, a statement of the amounts actually dispensed can be made using the embodiments shown in FIGS. 8 and 9. A warning signal can then be output, if a set dosage has not been completely dispensed and/or a dosage actually dispensed can be ascertained in order to dispense the amount still lacking in another administering process.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device configured to detect a position of a rotor relative to a stator for setting a dose of medicament, the rotor operatively coupled to a rod within an interior of the injection device, and the stator operatively coupled to a surface in the interior of the injection device, wherein the rotor is rotatable relative to the stator to effect dosage of the medicament, and at least one rotor electrode is arranged on said rotor and at least one stator electrode is arranged on said stator, such that said electrodes at least partially overlap in at least one position of the rotor relative to the stator, said at least one rotor electrode disposed on an exterior surface of the rotor and comprising an exterior rotor electrode surface that faces an interior portion of the stator, and said at least one stator electrode disposed on the interior portion of the stator and comprising an exterior stator electrode surface that faces the exterior surface of the rotor; and wherein a relative position of the rotor to the stator indicates a dosage and the injection device for detecting the position of the rotor relative to the stator provides an indication of the dosage as set.

2. The injection device as set forth in claim 1, wherein at least two electrodes are arranged on the stator.

3. The injection device as set forth in claim 1, wherein the at least one electrode on the rotor and the at least one electrode on the stator comprises a partially annular area of the rotor and stator respectively.

4. The injection device as set forth in claim 1, wherein the at least one electrode on the rotor and the at least one electrode on the stator are arranged such that, when the rotor is turned by a predetermined angle relative to the stator, the polarity of the electrodes can be reversed.

5. The injection device as set forth in claim 1, wherein the rotor is rotatable about the rod within the injection device.

6. The injection device as set forth in claim 1, wherein the rotor and rod are materially coupled and rotate within the injection device.

7. The injection device as set forth in claim 1, wherein the rotor comprises a plurality of rotational positions, each rotational position corresponding to the rotor electrode at least partially overlapping one electrode of a plurality of electrodes of the stator.

8. The injection device as set forth in claim 7, wherein each of the plurality of rotational positions is associated with a voltage.

9. The injection device as set forth in claim 8, wherein the voltages of each of the plurality of rotational positions are different from each other.

* * * * *